United States Patent
Shroff et al.

(10) Patent No.: US 8,680,011 B2
(45) Date of Patent: Mar. 25, 2014

(54) HERBICIDAL FORMULATION

(75) Inventors: Dipesh Kantisen Shroff, Mumbai (IN); Ashwin Champraj Shroff, Mumbai (IN); Ashok Kundanmal Jain, Mumbai (IN); Rajendra Pralhad Chaudhari, Mumbai (IN); Sanjay Dhirajlal Vadodaria, Mumbai (IN); Sanjay Shambhubhai Vaghela, Mumbai (IN); Vandana Chandrakant Mhatre, Mumbai (IN); Bhakti Rajesh Thakkar, Mumbai (IN)

(73) Assignees: Excel Crop Care Limited, Mumbai (IN); C C Shiroff Research Institute, Mumbai (IN)

( * ) Notice: Subject to any disclaimer, the term of this patent is extended or adjusted under 35 U.S.C. 154(b) by 303 days.

(21) Appl. No.: 12/865,700

(22) PCT Filed: Oct. 3, 2008

(86) PCT No.: PCT/IN2008/000636
§ 371 (c)(1),
(2), (4) Date: Nov. 1, 2010

(87) PCT Pub. No.: WO2009/098711
PCT Pub. Date: Aug. 13, 2009

(65) Prior Publication Data
US 2011/0045978 A1 Feb. 24, 2011

(30) Foreign Application Priority Data

Feb. 6, 2008 (IN) .......................... 253/MUM/2008

(51) Int. Cl.
*A01N 57/18* (2006.01)
*A01N 25/00* (2006.01)
*A61K 47/00* (2006.01)
*A61K 47/32* (2006.01)
*A01N 57/20* (2006.01)
*A01N 25/12* (2006.01)
*A01N 25/30* (2006.01)

(52) U.S. Cl.
USPC ..................... 504/206; 514/772.4; 514/785

(58) Field of Classification Search
USPC ................................ 504/206; 514/772.4, 785
See application file for complete search history.

(56) References Cited

U.S. PATENT DOCUMENTS

| 5,693,593 | A | * | 12/1997 | Arnold | 504/206 |
| 6,460,290 | B1 | * | 10/2002 | Moore et al. | 47/48.5 |
| 2004/0069032 | A1 | * | 4/2004 | Krysiak et al. | 71/27 |
| 2006/0247129 | A1 | * | 11/2006 | Bevinakatti | 504/206 |
| 2007/0225173 | A1 | | 9/2007 | Brigance et al. | |

FOREIGN PATENT DOCUMENTS

| EP | 0498145 | * | 8/1992 | A01N 57/20 |
| EP | 0498145 A1 | | 8/1992 | |
| EP | 0498185 | * | 8/1992 | A01N 57/20 |
| WO | WO01/10211 A1 | * | 2/2001 | A01N 25/08 |
| WO | WO2006/133788 A1 | * | 12/2006 | A01N 57/20 |
| WO | WO-2006133788 A1 | | 12/2006 | |

\* cited by examiner

*Primary Examiner* — Jane C Osweicki
(74) *Attorney, Agent, or Firm* — Birch, Stewart, Kolasch & Birch, LLP

(57) ABSTRACT

This invention relates to an improved granular formulation of herbicide glyphosate in form of ammonium salt using environmentally friendly adjuvants, and a process for preparation thereof. The formulation minimizes the use of some inactive ingredients without compromising the effectiveness of the product.

7 Claims, No Drawings

HERBICIDAL FORMULATION

This Application is the National Phase Under 35 U.S.C. §371 of PCT International Application No. PCT/IN2008/000636 which has an International filing date of Oct. 3, 2008, which claims priority to Indian Application No. 253/MUM/2008 filed on Feb. 6, 2008. The entire contents of all applications listed above are hereby incorporated by reference.

FIELD OF INVENTION

This invention relates to a granular formulation comprising ammonium salt of N-phosphonomethylglycine i.e., glyphosate, a process for manufacturing the same and use of said formulation for controlling weeds.

BACKGROUND AND PRIOR ART

N-(phosphonomethyl)glycine is a broad spectrum systemic non-selective herbicide generically known as Glyphosate. It is effective for control of annual and perennial plants including grasses, sedges, broad-leaved weeds and woody plants.

Glyphosate is commonly used in salt form such as isopropylamine salt, trimethylsulfonium salt, ammonium salt etc. However, the difference in efficacy of various brands is more likely to be due to the adjuvants used in the formulation and tank-mix rather than the type of salt itself. Many adjuvants are available to improve spreading, deposition and rain-fastness of glyphosate formulation.

The effectiveness of a formulation as well as its suitability from environmental point of view, both are important. Among the available adjuvants, those which are safe to the environment are preferable.

Ammonium sulfate is added to glyphosate formulations in order to improve its performance under stressful conditions, especially when hard water is used to prepare spray solution.

Various types of formulations of Glyphosate are commercially available such as suspension concentrate, water soluble or dispersible granules etc. The granular form is more popular and preferred over other forms.

Numerous compositions and processes have been disclosed in the literature for preparation of granular formulation of ammonium glyphosate using various adjuvants. These include patents/applications viz. WO9007275, EP252897, WO2007112933, WO2006133788, JP2005112836, US2004102323, U.S. Pat. No. 5,858,921, WO9800022, EP0378985 and EP0582561. Tallow amine surfactants are most commonly used in these glyphosate formulations. European patent EP0378985 discloses a granular formulation of glyphosate salt in which the most preferred surfactant is an ethoxylated tallow amine containing 15-18 moles of ethylene oxide. WO2006133788 describes a process for preparing water-soluble ammonic glyphosate granules in which tallow amine surfactant is preferably used.

Though glyphosate itself is practically non-toxic to fish, the toxicity is due to tallow amine surfactant used in the formulation. Therefore such formulations are not suitable for use in or close to aquatic environment. Tallow amine surfactants are also irritants to eyes & skin. Therefore it is preferable to have a glyphosate formulation in which non-tallow amine surfactants are used.

U.S. Pat. No. 6,248,695 discloses herbicidal composition comprising glyphosate or its salt and an alkyldiamine tetraalkoxylate surfactant. It also claims the use of alkyl glycoside or alkyl polyglycoside surfactants along with alkyldiamine tetraalkoxylate in glyphosate or its salt containing composition. However, in the said patent, the surfactant requirement is as high as 21-22 wt %. In the formulation described in said patent, alkyl glycoside or alkyl polyglycoside is not used without using alkyldiamine tetraalkoxylate simultaneously. Moreover, in the said patent, the formulation of isopropylamine salt of glyphosate is in liquid form when alkyl glycoside is used.

The use of alkyl glycoside or alkyl polyglycoside surfactants in granular formulation of ammonium salt of glyphosate is not known in the art.

OBJECTS OF INVENTION

The main object of this invention is to provide a cost-effective granular formulation of glyphosate without using tallow amine surfactant.

Another object of invention is to provide a formulation of ammonium glyphosate in granular form using alkyldiamine alkoxylate and alkyl glycoside or alkyl polyglycoside surfactants.

Another object of invention is to provide an environmentally safer formulation of glyphosate.

Another object of invention is to minimize the use of inactive ingredients without compromising the effectiveness of the product.

Another object of the invention is to provide a process for preparation of granular formulation of ammonium glyphosate using alkyl glycoside or alkyl polyglycoside surfactants and alkyldiamine alkoxylate surfactants.

Another object of invention is to provide a method of weed control using the formulation of this invention.

SUMMARY OF INVENTION

The present invention relates to a novel granular formulation of ammonium salt of glyphosate, method of preparation thereof and use of said formulation for controlling weeds. In the formulation of present invention, non-toxic surfactants such as alkyldiamine alkoxylate, alkyl-glycoside/polyglycoside etc. have been used.

DETAILED DESCRIPTION OF INVENTION

Though the use of alkyldiamine alkoxylate in granular formulation of ammonium glyphosate is reported in U.S. Pat. No. 6,248,695, the amount of surfactant which has to be used therein is as high as 21-22 wt %. On the other hand, in the formulation of present invention, only 11-12 wt % of this surfactant is required and as little as 1.1 wt % of water soluble acrylate based copolymer is required. This reduces environmental load of inactive ingredients and at the same time it gives scope to add other desired ingredients. The role of each adjuvant used in the present invention is as described hereinafter.

Alkyl polyglycoside surfactant used in the present invention exhibit low surface tension, good wettability, they are non-toxic, non-irritant, environmentally friendly and biodegradable. Due to their safe characteristics, they are also used in cosmetic compositions. C6-12 Alkyl polyglycosides are preferred surfactants and C8-C10 alkyl polyglycosides are most preferred surfactants. Even mixtures containing variable alkyl chain can be used such as C6 & C8 alkyl-, C8 & C10 alkyl-, and C8 & C12 alkyl-polyglycosides etc.

The binder(s) used in the said formulation are based on water-soluble acrylate based co-polymers. Some examples include but not limited to acrylic acid or methacrylic acid ester-acrylic acid copolymers, wherein the ester may be selected from ethyl, butyl, isobutyl, n-hexyl, n-octyl, lauryl, 2-ethylhexyl and stearyl acrylates. In addition to these, acrylamide-acrylic acid, ethyl acrylate copolymer with methyl methacrylate, methacrylic acid polymer with butyl acrylate can also be used.

Fatty amine ethoxylate surfactant is used in a comparative example.

Ethylenediamine alkoxylate such as ethylenediamine ethoxylate or 1,2-Ethanediamine Polymer With Methyl Oxirane and Oxirane can also be used in the formulation of present invention along with water soluble acrylate based copolymer. Ethylenediamine alkoxylates are approved by EPA reassessment process and are listed on the new 40CFR 180.960 polymers and exempted from the requirement of tolerance data. Ethylenediamine alkoxylates are considered to be low risk under 40CFR 723.250 and no mammalian toxicity is anticipated from dietary, inhalation, or dermal exposure to this compound.

The process for preparation of granular formulation of ammonium glyphosate in accordance with the present invention involves the steps of taking ammonium glyphosate, ammonium sulfate and adjuvants in required quantity in the mixer, adding water to make dough, mixing for half an hour to get uniform dough, extruding the dough to get granules and drying the granules at 40-65° C. Each specific example with quantities of ingredients is described below.

Example-1

71 wt % ammonium glyphosate, 19.69 wt % ammonium sulfate, 8.26 wt % C8-10 alkyl polyglycoside and 1.1 wt % acrylate based copolymer were taken in the mixer. Water was added for making dough. The contents were mixed for half an hour to get uniform dough. The dough was extruded to obtain granules which were dried at 60-65° C. The granules thus obtained were free-flowing and soluble in water.

Example-2

71 wt % ammonium glyphosate, 21.5 wt % ammonium sulfate, 5.9 wt % C8-10 alkyl polyglycoside and 1.6 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-3

71 wt % ammonium glyphosate, 20.9 wt % ammonium sulfate, 7.0 wt % 1,2-Ethanediamine Polymer With Methyl Oxirane & Oxirane and 1.1 wt % acrylate based copolymer were taken in the mixer. Water was added to make dough. The contents were mixed for half an hour to get uniform dough. The dough was extruded to obtain granules which were dried at 40° C. The granules thus obtained were free-flowing and soluble in water.

Example-4

71 wt % ammonium glyphosate, 16.1 wt % ammonium sulfate, 11.8 wt % 1,2-Ethanediamine, Polymer With Methyl Oxirane and Oxirane and 1.1 wt % acrylate based copolymer were taken in the mixer. Water was added to make dough. The contents were mixed for half an hour to get uniform dough. The dough was extruded to obtain granules which were dried at 40° C. The granules thus obtained were free-flowing and soluble in water.

Example-5

Comparative Example 71 wt % ammonium glyphosate, 16.1 wt % ammonium sulfate, 11.8 wt % fatty amine ethoxylate and 1.1 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-6

71 wt % ammonium glyphosate, 17 wt % ammonium sulfate, 10.5 wt % C8-10 alkyl polyglycoside and 1.5 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-7

71 wt % ammonium glyphosate, 20 wt % ammonium sulfate, 7.5 wt % C8-10 alkyl polyglycoside and 1.5 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-8

71 wt % ammonium glyphosate, 12.5 wt % ammonium sulfate, 15 wt % 1,2-Ethanediamine, Polymer With Methyl Oxirane and Oxirane and 1.5 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-9

71 wt % ammonium glyphosate, 12.5 wt % ammonium sulfate, 15 wt % fatty amine ethoxylate and 1.5 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-10

71 wt % ammonium glyphosate, 15.5 wt % ammonium sulfate, 10.5 wt % C8-10 alkyl polyglycoside and 3.0 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing but hard in nature and soluble in water.

Example-11

71 wt % ammonium glyphosate, 18.5 wt % ammonium sulfate, 7.5 wt % C8-10 alkyl polyglycoside and 3.0 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing but hard in nature and soluble in water.

Example-12

71 wt % ammonium glyphosate, 11 wt % ammonium sulfate, 15 wt % 1,2-Ethanediamine, Polymer With Methyl Oxirane and Oxirane, and 3.0 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing but hard in nature and soluble in water.

Example-13

71 wt % ammonium glyphosate, 11 wt % ammonium sulfate, 15 wt % fatty amine ethoxylate and 3.0 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing but hard in nature and soluble in water.

Example-14

71 wt % ammonium glyphosate, 15.4 wt % ammonium sulfate, 12.5 wt % C8-10 alkyl polyglycoside and 1.1 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-15

60 wt % ammonium glyphosate, 31.1 wt % ammonium sulfate, 5.9 wt % C8-10 alkyl polyglycoside and 3.0 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-16

85 wt % ammonium glyphosate, 1.5 wt % ammonium sulfate, 10.5 wt % C8-10 alkyl polyglycoside and 3.0 wt % acrylate based copolymer were taken in the mixer. Water was added to make dough. The contents were mixed for half an hour to get uniform dough. The dough was extruded to obtain granules which were dried at 60-65° C. The granules thus obtained were free-flowing and soluble in water.

Example-17

71 wt % ammonium glyphosate, 15.4 wt % ammonium sulfate and 12.5 wt % C8-10 alkyl polyglycoside were taken in the mixer. Water was added to make dough. The contents were mixed for half an hour to get uniform dough. The dough was extruded to obtain granules which were dried at 60-65° C. The granules thus obtained were soft and brittle in nature.

The formulation of this invention as described in Examples 1-14 can be used for controlling weeds by spraying aqueous solution of 2-4 Kg formulation per Ha. The optimum dose depends on the weed density. A dose rate of 3 Kg/Ha is generally sufficient. The formulation is more effective if sprayed after weeds develop some leaves. Formulation as described in other Examples can be used in an identical manner, by taking the quantity equivalent to that in Examples 1-14 in terms of the active ingredient.

The invention claimed is:

1. A granular formulation comprising 60-85 wt % of ammonium glyphosate, 1.5-32 wt % ammonium sulfate, 5-12.5 wt % of one or more C6-C12 alkyl(poly)glycosides and 1-3 wt % acrylate based copolymer.

2. A process for preparing a granular formulation comprising the steps of adding 60-85 wt % ammonium glyphosate, 1.5-32 wt % ammonium sulfate, 5-12.5 wt % of one or more C6-C12 alkyl(poly)glycosides and 1-3 wt % acrylate based copolymer, adding water while mixing until the mixture results into an extrudable dough and mixing for half an hour to obtain a uniform dough, extruding the dough to get granules and drying the granules at 38-65° C.

3. A method of controlling weeds by spraying an aqueous solution of the granular formulation according to claim 1.

4. A method of controlling weeds according to claim 3, wherein said formulation is sprayed at a dose of 2-4 Kg/Ha.

5. A method of controlling weeds by spraying an aqueous solution of a granular formulation which is prepared by the process according to claim 2.

6. A granular formulation as claimed in claim 1, wherein said alkyl polyglycoside is selected from C8-C10 alkyl polyglycoside.

7. A granular formulation prepared in accordance with the process of claim 2, wherein said alkyl(poly)glycoside is at least one C8-C10 alkyl polyglycoside.

* * * * *